United States Patent [19]

Kurwa

[11] Patent Number: 5,662,668

[45] Date of Patent: Sep. 2, 1997

[54] BLADE FOR INTRASTROMAL RADIAL KERATOTOMY

[76] Inventor: Badrudin Kurwa, 1035 Singlewood Dr., Arcadia, Calif. 91006

[21] Appl. No.: 427,404

[22] Filed: Apr. 24, 1995

[51] Int. Cl.$^6$ ........................................ A61F 9/00
[52] U.S. Cl. ................................ 606/166; 606/107
[58] Field of Search ........................ 606/166, 167, 606/168, 107, 205, 170, 172

[56] References Cited

U.S. PATENT DOCUMENTS

| 5,203,865 | 4/1993 | Siepser ................ 606/166 |
| 5,222,967 | 6/1993 | Casebeer et al. ......... 606/166 |
| 5,224,950 | 7/1993 | Prywes ................. 606/166 |
| 5,376,099 | 12/1994 | Ellis et al. ............. 606/166 |

OTHER PUBLICATIONS

Article entitled "What's New in Refractive Surgery Instruments", *Review of Ophthalmology* (A Chilton Publication), Jun. 1995, cover page, table of contents, editor's page, and pages 60–67 (total 9 pages).

*Primary Examiner*—Michael Buiz
*Assistant Examiner*—Kevin Truong
*Attorney, Agent, or Firm*—John J. Connors; Connors & Assoc.

[57] ABSTRACT

The horizontal base of an L-shaped blade is inserted within an existing incision performed as part of a traditional radial keratotomy procedure to permit an intrastromal cut to be made to urge corneal collapse and provide myopia correction without incurring glare and central vision distortion for the patient. The base of the blade extends approximately 1 mm to a very sharp vertical edge from the vertical arm attached to a blade holder to permit up to an equivalent length intrastromal cut until the end of the arm reaches the end of the preexisting incision through Bowman's membrane and the epithelium. The height of the base and length of the cutting edge is approximately 450 microns to prevent cutting or perforation of either of Bowman's or Descemet's membranes.

18 Claims, 2 Drawing Sheets

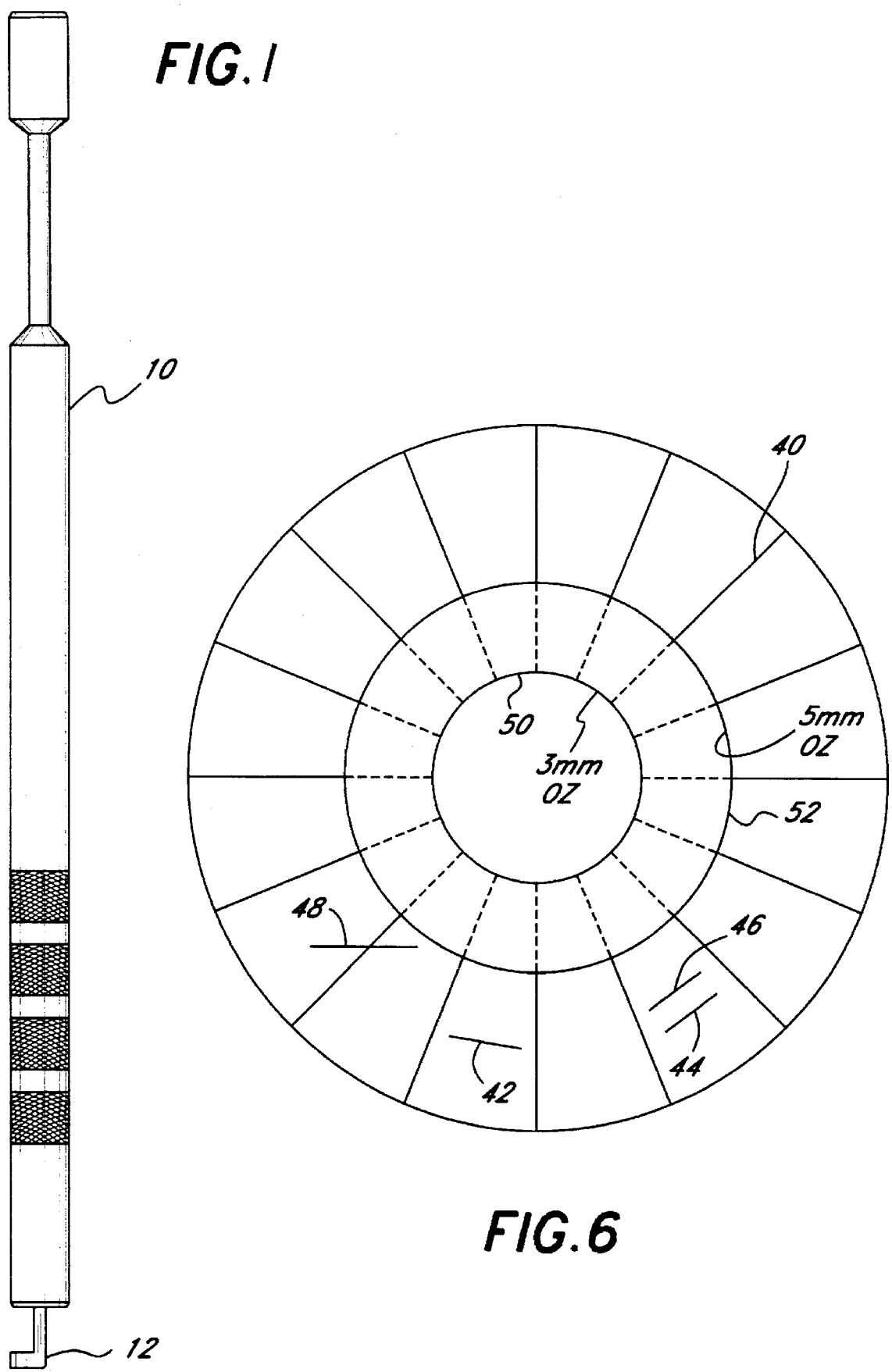

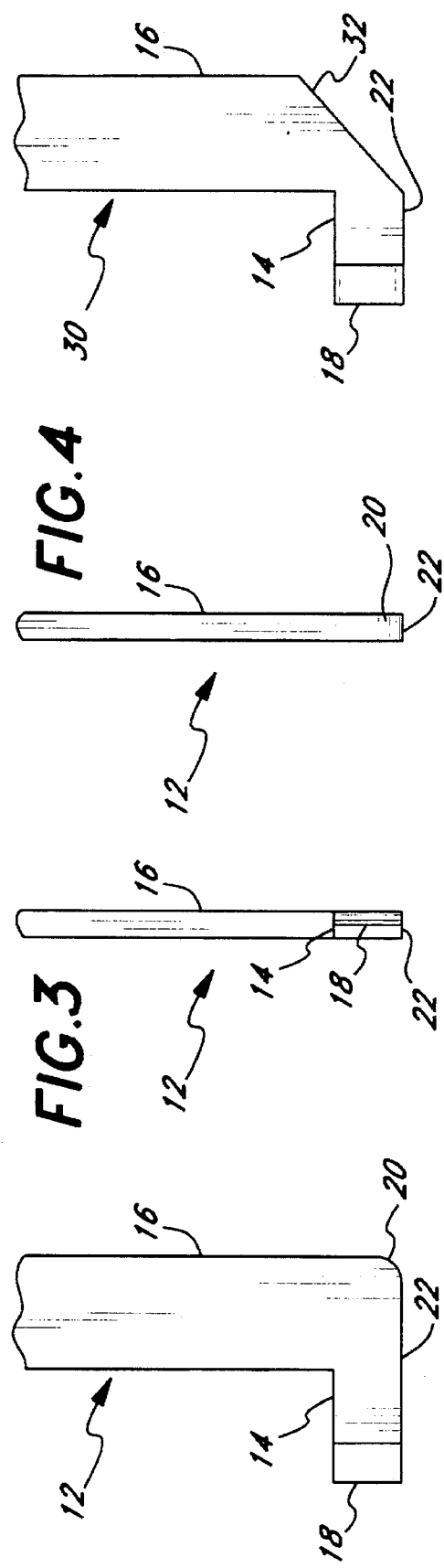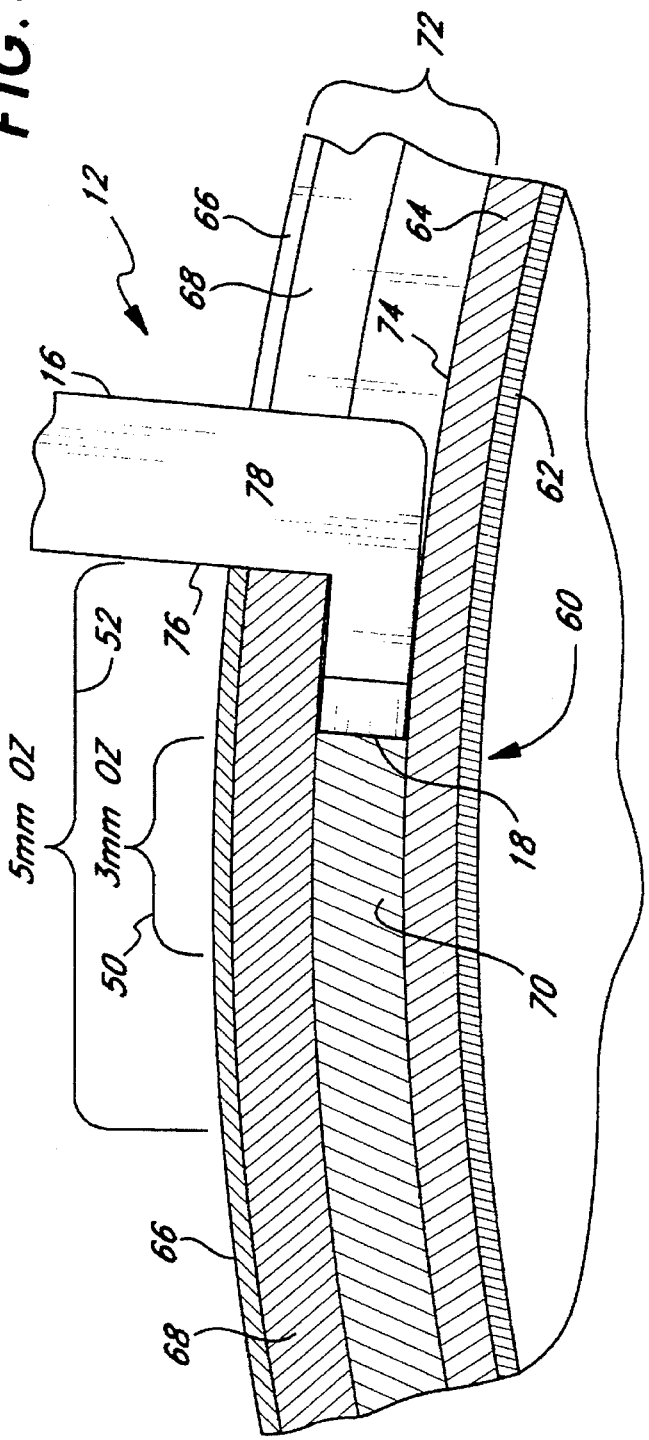

BLADE FOR INTRASTROMAL RADIAL KERATOTOMY

BACKGROUND OF THE INVENTION

1. Field of the Invention

The present invention relates to a blade for use in a radial keratotomy procedure and, more particularly, to a blade for making an intrastromal incision within a cornea.

2. Description of Related Art

Radial keratotomy is a procedure first performed in the 1950's to achieve corneal flattening to correct myopia. Significant advances have been made since the mid-1970's with respect to corneal mapping, instruments and type and nature of incisions to be made to improve the vision of patients. Generally, four or eight evenly spaced incisions extending radially from a predetermined optical zone are made. To correct certain problems of astigmatism, a variety and number of transverse incisions may be made.

The main function of radial keratotomy is that of achieving corneal flattening to correct myopia; correction of astigmatism may also be achieved in appropriate situations. If the incisions extend into or are close to the optical zone, glare and distortion may be present. The degree of glare and distortion may also be a function of the degree of intensity of the ambient light. Generally, more effective corneal flattening is achieved the further into the optical zone the incisions are made but such intrusions may result in unacceptable side effects to the patient. Accordingly, the degree of correction to be made must be tempered by the overall benefit to the patient.

SUMMARY OF THE INVENTION

After a traditional radial keratotomy procedure has been performed, the incisions normally end at the edge of a predetermined optical zone. The horizontal base of an L-shaped blade is inserted into an incision to rest on the groove formed. The base of the blade extends approximately 1 mm from the arm of the blade and is terminated by a very sharp vertical apex or edge of approximately 450 microns in length. In this position, the base (and cutting edge) is located between Bowman's and Descemet's membranes. Radial movement of the blade toward the optical center will incise the stroma but leave Bowman's and Descemet's membranes intact. The resulting incision formed to a greater or lesser extent within the optical zone will result in further corneal flattening but avoid creation of any further glare or vision distortion as Bowman's membrane remains intact within the optical zone. This procedure can also be used to enhance an existing undercorrection of a previously performed radial keratotomy procedure.

It is therefore a primary object of the present invention to provide additional myopic correction through radial keratotomy without adding glare or central vision distortion.

Another object of the present invention is to provide a blade for performing intrastromal radial keratotomy.

Yet another object of the present invention is to provide a blade for performing a cut within the optical zone but without incising the epithelium or Bowman's membrane.

Still another object of the present invention is to provide a configuration of a blade for intrastromal radial keratotomy that self limits the extent of an intrastromal cut that can be made.

A further object of the present invention is to provide a diamond L-shaped blade for making intrastromal cuts to produce corneal flattening.

A yet further object of the present invention is to provide a cutting edge disposed between Bowman's and Descemet's membranes for making intrastromal cuts.

A still further object of the present invention is to provide a method for providing additional correction for myopia without adding glare or central vision distortion.

A still further object of the present invention is to provide a method for making intrastromal incisions within a cornea.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which:

FIG. 1 illustrates a blade holder for supporting a blade to be used for intrastromal radial keratotomy;

FIG. 2 is a side view of the blade;

FIG. 3 is a front view of the blade;

FIG. 4 is a rear view of the blade;

FIG. 5 illustrates a variant configuration of the blade shown in FIG. 2;

FIG. 6 is a plan view illustrating the optical zone and various incisions that might be made in a cornea as part of a radial keratotomy procedure; and FIG. 7 is a cross-sectional view of a representative cornea and illustrating use of the blade of the present invention to make an intrastromal cut.

DETAILED DESCRIPTION OF THE PREFERRED EMBODIMENTS

In the 1950's when SATO (Japan) did his original radial keratotomy (RK) incisions, they were done from the endothelial side of the cornea. He used a special blade to cut from inside to outside dividing the endothelium, Descemet's membrane and the stroma leaving Bowman's membrane and the epithelium intact (presumably to protect against infections). Since the importance of the endothelium is now better understood, the modern RK approach is to go through the epithelium, Bowman's membrane, and the stroma in order to keep Descemet's membrane and the endothelium intact. The main objection to this approach is that glare and central vision distortion become noticeable if the radial incisions are carried too far centrally. While thinking through this evolutionary process, the inventor developed the hypothesis that perhaps it may not be necessary to incise or divide either the Bowman's membrane or the Descemet's membrane to achieve corneal flattening. And, perhaps, the desired corneal flattening could be achieved by making incisions only through the corneal stroma in and proximate the optical zone. The inventor thereafter began to devise a blade that could perform such intrastromal cuts and to develop the procedures for using such a blade.

Referring to FIG. 1, there is illustrated a blade holder 10 supporting a blade 12 for use in making intrastromal cuts in the cornea as part of a radial keratotomy procedure. It is to be noted that the blade and blade holder are not to scale and are depicted for illustrative purposes only. Ophthalmologists and those skilled in the art of instruments for use in RK procedures will readily appreciate and understand that various mechanisms may be employed to removably engage the blade with the blade holder; moreover, it may be advantageous to mount the blade holder in an existing handle presently in use or in a to-be-developed handle or use the blade holder in the manner of a handle. Moreover, these persons will also readily understand how to manipulate the blade holder/handle in order to cause the blade to perform its intended surgical function.

Blade 12 will be described with greater specificity with joint reference to FIGS. 2, 3, and 4. The blade is L-shaped and includes a horizontal base 14 extending from a vertical arm 16. The end or apex of the base is terminated by a vertical edge 18 sharpened (or faceted) to the highest degree possible. Preferably, edge 18 is a diamond edge brazed to base 14 if the base and arm are of stainless steel or of material other than diamond. That is, the blade may be of stainless steel, tungsten carbide, ceramic, sapphire or other suitable material. Recent work on the blade has suggested that the whole blade be of diamond, in which case edge 18 would be formed by faceting.

The purpose of blade 12 is that of augmenting an existing RK incision to cut the stroma lamellae without a commensurate cut in Bowman's membrane or in the epithelium. Thus, blade 12 is dimensioned for such specific purpose. Since such augmenting cuts to be made are on the order of 0.5 to 1 millimeters in length, the length of base 14 extending from arm 16 should be no more than 1 millimeter. Preferably, the length of the base should be commensurate with the length of the cut to be made. Such dimension will limit the length of the cut to the length of the base as the arm will interferingly engage with the end of the incision existing in Bowman's membrane. To ensure against perforation or cutting of Descemet's membrane or Bowman's membrane, the height of base 14 (and vertical length of the cutting edge) should be somewhat less than the thickness of the stroma; investigations to date suggest a height of about 450 microns since the thickness of most corneas is 500+ microns. While the cutting edge is illustrated as being vertical, it can be forwardly or rearwardly slanted to accommodate special procedures that may exist or may be developed. The thickness of the blade, or at least of base 14, is preferably about 0.17 millimeters. The width of arm 16 should be kept to 1 millimeter or less (possibly 0.75 or 0.50 millimeters consistent with the required structural strength). The preferred length of the arm should be on the order of 3.5 to 6 millimeters. To prevent injury at the bottom of the incision upon removal of blade 12, the bottom rear corner 20 is preferably slightly beveled, or rounded as indicated. If the blade is of diamond, the corner can be polished if it is bevelled; if the corner is rounded by a laser cut, it will be rough. Furthermore, lower edge 22 of base 14 should be polished to minimize drag and enhance travel along the groove of the incision.

A variant 30 of blade 12 is illustrated in FIG. 5. In this variant, the length of lower edge 22 is significantly reduced by sloping rear edge 32. Because of the shortened lower edge, unwanted rocking of the blade may occur. If the height of blade 12 is significantly less than the intrastromal depth, the possibility of rocking the blade may be used to advantage to permit varying or variable depth cuts to be made to accommodate or conform with unique procedures or procedures to be developed.

FIG. 6 depicts a planform of incisions potentially to be made in the cornea, as will be dictated by the specific RK procedure(s) to be performed. That is, 4, 8, or even 16 radial incisions 40 may be made. Alternatively, or in combination, transverse incisions 42, parallel incisions 44,46, angled incisions 48 or specific pattern incisions (not illustrated) may be made. The type and nature of incisions will primarily be dictated by the topography of the cornea and other factors well known to ophthalmologists practicing RK.

Through the use of blade 12, in combination with a traditional RK procedure, and assuming that an optical zone 50 of 3 millimeters is dictated, the following heretofore unavailable procedure could be undertaken. Traditional radial incisions made with a conventional RK blade would extend only to a 5 millimeter optical zone 52. Each of these incisions would be extended intrastromally by inserting base 14 of blade 12 into each incision and centrally extending it between Bowman's membrane and Descemet's membrane from the perimeter of the 5 millimeter optical zone 52 for a distance of 1 millimeter to the perimeter of the 3 millimeter optical zone 30. Thereby, the 5 millimeter optical zone would have an intact Bowman's membrane and epithelium without the otherwise associated glare and central vision distortion; moreover, patient recovery would be proportionately more rapid.

In the event an initial RK procedure to a 3 millimeter optical zone results in one diopter or less of undercorrection, the correction can be enhanced through use of blade 12. In such situation, the original RK incisions are prised open to a radial length of approximately 1.5 millimeters. Blade 12 is placed into the incision until bottom edge 22 rests along the groove of the incision. By advancing the blade toward the center of the cornea, the cutting edge, facing the corneal center, will cut the intrastromal lamellae under Bowman's membrane to cause collapse of the corneal zone. The optical zone would be reduced to approximately 2 millimeters, or to the extent controlled by the surgeon or by the interference between the front edge of arm 16 and the end of the original incision through Bowman's membrane. By selecting a blade 12 having a specific length base 14, essentially absolute control over the length of the intrastromal cut to be made can be controlled due to the interference between arm 16 and the end of the original incision. It has also been learned that transverse incisions can be extended across an existing incision by cutting only the stroma and not Bowman's membrane (note incision 48). Thereby, gaping of Bowman's membrane and the epithelium at the intersection is prevented.

Referring to FIG. 7, there is illustrated a partial representative cross-sectional view of a cornea 60. An endothelial layer 62 is adjacent Descemet's membrane 64. An epithelial layer 66 is adjacent Bowman's membrane 68. Stroma 70 is disposed between Bowman's and Descemet's membranes and is of a thickness somewhat greater than 450 microns. Using a conventional RK blade and traditional RK procedure an incision 72 through epithelial layer 66, Bowman's membrane 68 and stroma 70 is made radially centrally to a 5 millimeter optic zone (OZ); this zone is represented by numeral 52 in FIGS. 6 and 7.

Assuming that the procedure dictated an optic zone (OZ) of 3 millimeters (as represented by numeral 50), blade 12 is inserted into incision 72 until it rests upon groove 74 at the bottom of the incision adjacent or close to Descemet's membrane. Translating blade 12 radially centrally, will result in edge 18 performing a cut through stroma 70 in radial alignment with incision 72. The length of this cut can be controlled by the physician if his hand is sufficiently steady and he has developed the requisite skill. Alternatively, the length of the cut can be selected by employing a blade 12 having a base 14 extending from arm 16 a distance commensurate with the length of the cut to be made. Then, upon translation of blade 12 centrally radially within incision 72, translation will be inhibited upon interference between the leading edge 76 of arm 16 with end 78 of incision 72. By having base 14 extend for 1 millimeter from leading edge 76 of arm 16, the cut made will be 1 millimeter long and the original incision will be extended through the stroma to the perimeter of the 3 millimeter optic zone (OZ), as represented by numeral 50 in FIGS. 6 and 7.

The above described procedure for extending incisions or cuts through only the stroma of radial incisions can be equally and similarly applied to other non radial incisions, irrespective of their orientation. Again, the length of such extended incisions or cuts in the stroma can be a function of the skill of the surgeon or more pragmatically dictated by the length of the base of the blade. Furthermore, the depth of the extension cut to be made is a function of the height of the base of the blade and specific procedures can be developed to take advantage of such facility.

While the invention has been described with reference to several particular embodiments thereof, those skilled in the art will be able to make the various modifications to the described embodiments of the invention without departing from the true spirit and scope of the invention. It is intended that all combinations of elements and steps which perform substantially the same function in substantially the same way to achieve the same result are within the scope of the invention.

What is claimed is:

1. A blade for a keratotomy procedure adapted to make an intrastromal incision in stromal lamellae intermediate Descemet's and Bowman's membranes which are separated from each other by a predetermined distance, said blade being placed in a radial incision through an epithelial layer of a cornea which has a distal end terminating at an edge of a central optic zone in the cornea and a bottom near Descemet's membrane, said blade including a base and an arm which are substantially flat members connected together edgewise to lie in essentially the same plane and are thin so that said base and arm fit edgewise within said radial incision, said base having non-cutting bottom and top edges separated by a distance which is less than said predetermined distance between Descemet's and Bowman's membranes, said non-cutting top edge terminating at a distal end at a cutting edge and at a proximal end at a junction formed between the base and a non-cutting leading edge of the arm, and the bottom edge terminating at a distal end at said cutting edge and at a proximal end connected to the arm, said non-cutting leading edge of the arm acting as a stop upon inserting the base into the radial incision with the bottom edge adjacent the bottom of the radial incision and advancing the cutting edge towards the optic zone so that the non-cutting leading edge engages the distal end of the radial incision, said cutting edge extending between the non-cutting bottom and top edges, with the distance between the cutting edge and the non-cutting leading edge of the arm being sufficient to enable the cutting edge to extend the radial incision inward towards the optic zone and beyond said distal end of the radial incision to make an intrastromal incision in the stromal lamellae intermediate Descemet's and Bowman's membranes but beneath the central optic zone in the epithelial layer of the cornea without cutting Bowman's membrane.

2. The blade of claim 1 where said non-cutting bottom and top edges are substantially parallel to each other.

3. The blade of claim 1 where said base and arm are substantially at a right angle with respect to each other, with the cutting edge being essentially at a right angle to the non-cutting bottom and top edges.

4. The blade of claim 1 where said base and arm have an L-shape configuration.

5. The blade of claim 1 where the distance between said distal end of the top edge of the base and said junction formed between the base and the non-cutting leading edge of the arm is no more than 1.5 millimeters.

6. The blade of claim 1 where said arm is no more than 1 millimeter wide and the distance between said distal end of the top edge of the base and said junction formed between the base and the non-cutting leading edge of the arm is at least 0.5 millimeter.

7. The blade of claim 1 where the cutting edge has an effective length to make at least 400 micron wide incision extending between Descemet's and Bowman's membranes.

8. The blade of claim 1 where the cutting edge is approximately 450 microns.

9. The blade of claim 1 where the base has a thickness of no more than 200 microns.

10. The blade of claim 1 where the base has a trailing edge which is sloped to reduce the length of the bottom edge.

11. The blade of claim 1 where there is a blade holder attached to the arm.

12. A blade for a keratotomy procedure adapted to make an intrastromal incision in stromal lamellae intermediate Descemet's and Bowman's membranes which are separated from each other by a predetermined distance, said blade being placed in a radial incision through an epithelial layer of a cornea which has a distal end terminating at an edge of a central optic zone in the cornea and a bottom near Descemet's membrane, said blade including a base and an arm which are substantially flat members connected together edgewise to lie in essentially the same plane and are thin having a thickness of no more than 200 microns so that said base and arm fit edgewise within said radial incision with the base extending lengthwise in the incision, said base having non-cutting bottom and top edges connected by opposed substantially flat, parallel, non-cutting sides, said non-cutting bottom and top edges being substantially parallel to each other and separated by a distance which is less than said predetermined distance between Descemet's and Bowman's membranes, said non-cutting top edge terminating at a distal end at a cutting edge and at a proximal end at a junction formed between the base and a non-cutting leading edge of the arm, said cutting edge being the only cutting edge on the blade, said distal end of the top edge of the base and said junction formed between the base and the non-cutting leading edge of the arm separated by a distance of from 0.5 to 1.5 millimeters, said bottom edge terminating at a distal end at said cutting edge and at a proximal end connected to the arm, said non-cutting leading edge of the arm acting as a stop upon inserting the base into the radial incision with the bottom edge adjacent the bottom of the radial incision and advancing the cutting edge towards the optic zone so that the non-cutting leading edge engages the distal end of the radial incision, said cutting edge extending between the non-cutting bottom and top edges and having an effective length to make at least 400 micron wide incision extending between Descemet's and Bowman's membranes.

13. The blade of claim 12 where said base and arm are substantially at a right angle with respect to each other, with the cutting edge being essentially at a right angle to the non-cutting bottom and top edges.

14. The blade of claim 13 where said base and arm have an L-shape configuration.

15. The blade of claim 14 where said arm is no more than 1 millimeter wide.

16. The blade of claim 15 where the cutting edge is approximately 450 microns.

17. The blade of claim 16 where the base has a trailing edge which is sloped to reduce the length of the bottom edge.

18. A keratotomy procedure for making an intrastromal incision in stromal lamellae of a cornea intermediate Descemet's and Bowman's membranes which are separated from each other by a predetermined distance, said procedure including (a) making a radial incision through an epithelial layer of the cornea which has a distal end terminating at an edge of a central optic zone in the cornea and a bottom near Descemet's membrane, (b) providing a blade including a base and an arm which are substantially flat members connected together edgewise to lie in essentially the same plane and are thin so that said base and arm fit edgewise within said radial incision, said base having non-cutting bottom and top edges separated by a distance which is less than said predetermined distance between Descemet's and Bowman's membranes, said non-cutting top edge terminating at a distal end at a cutting edge and at a proximal end at a junction formed between the base and a non-cutting leading edge of the arm, and the bottom edge terminating at a distal end at said cutting edge and at a proximal end connected to the arm, said non-cutting leading edge of the arm acting as a stop upon inserting the base into the radial incision with the bottom edge adjacent the bottom of the radial incision and advancing the cutting edge towards the optic zone so that the non-cutting leading edge engages the distal end of the radial incision, said cutting edge extending between the non-cutting bottom and top edges, with the distance between the cutting edge and the non-cutting leading edge of the arm being sufficient to enable the cutting edge to extend the radial incision inward towards the optic zone and beyond said distal end of the radial incision to make an intrastromal incision in the stromal lamellae intermediate Descemet's and Bowman's membranes but beneath the central optic zone in the epithelial layer of the cornea without cutting Bowman's membrane, (c) inserting the blade into the radial incision placing the base and arm edgewise within said radial incision with the base extending lengthwise in the incision and the bottom edge of the base adjacent the bottom of the incision, and (d) advancing the cutting edge of the blade towards the center of the optic zone until the leading edge of the arm engages the distal end of the radial incision to make an intrastromal incision in the stromal lamellae intermediate Descemet's and Bowman's membranes but beneath the central optic zone in the epithelial layer of the cornea without cutting Bowman's membrane.

* * * * *